United States Patent
Ranck et al.

(10) Patent No.: US 8,226,654 B2
(45) Date of Patent: Jul. 24, 2012

(54) TROCAR-TIPPED DRILL BIT

(75) Inventors: Roger S. Ranck, Ambler, PA (US); Robert S. Kramer, Cherry Hill, NJ (US); Anatoli Krivoruk, Philadelphia, PA (US)

(73) Assignee: Aeton Medical LLC, Spring House, PA (US)

( * ) Notice: Subject to any disclaimer, the term of this patent is extended or adjusted under 35 U.S.C. 154(b) by 777 days.

(21) Appl. No.: 12/328,310

(22) Filed: Dec. 4, 2008

(65) Prior Publication Data

US 2010/0145341 A1   Jun. 10, 2010

(51) Int. Cl.
*A61B 17/00* (2006.01)
(52) U.S. Cl. .......................... 606/80; 606/167
(58) Field of Classification Search .............. 606/72, 606/77–90, 167
See application file for complete search history.

(56) References Cited

U.S. PATENT DOCUMENTS

| | | | | |
|---|---|---|---|---|
| 5,051,092 A | * | 9/1991 | Miller | 433/225 |
| 5,338,197 A | * | 8/1994 | Kwan | 433/174 |
| 5,354,299 A | * | 10/1994 | Coleman | 606/916 |
| 5,374,270 A | | 12/1994 | McGuire et al. | |
| 5,522,817 A | * | 6/1996 | Sander et al. | 606/329 |
| 5,617,854 A | * | 4/1997 | Munsif | 600/374 |
| 5,645,547 A | * | 7/1997 | Coleman | 606/304 |
| 5,741,267 A | | 4/1998 | Jorneus et al. | |
| 5,816,812 A | * | 10/1998 | Kownacki et al. | 433/174 |
| 5,895,425 A | * | 4/1999 | Grafton et al. | 606/304 |
| 5,941,706 A | | 8/1999 | Ura | |
| 6,045,497 A | * | 4/2000 | Schweich et al. | 600/16 |
| 6,068,479 A | | 5/2000 | Kwan | |
| 6,210,432 B1 | * | 4/2001 | Solem et al. | 623/1.15 |
| 6,306,140 B1 | * | 10/2001 | Siddiqui | 606/315 |
| 6,402,781 B1 | * | 6/2002 | Langberg et al. | 623/2.36 |
| 6,478,776 B1 | * | 11/2002 | Rosenman et al. | 604/164.01 |
| 6,556,873 B1 | * | 4/2003 | Smits | 607/122 |
| 6,602,288 B1 | * | 8/2003 | Cosgrove et al. | 623/2.36 |
| 6,626,887 B1 | * | 9/2003 | Wu | 604/512 |
| 6,863,529 B2 | * | 3/2005 | Strong et al. | 433/165 |
| 6,997,951 B2 | * | 2/2006 | Solem et al. | 623/2.37 |
| 7,048,477 B2 | | 5/2006 | Abrams | |
| 7,186,264 B2 | * | 3/2007 | Liddicoat et al. | 623/2.37 |
| 2002/0031745 A1 | | 3/2002 | Kumar et al. | |
| 2002/0172923 A1 | * | 11/2002 | Strong et al. | 433/165 |
| 2003/0235805 A1 | | 12/2003 | Lax | |
| 2005/0169720 A1 | | 8/2005 | Kobayashi | |
| 2007/0099150 A1 | | 5/2007 | Muller et al. | |
| 2007/0298375 A1 | | 12/2007 | Hirsch et al. | |
| 2008/0154304 A1 | | 6/2008 | Crawford et al. | |
| 2008/0167653 A1 | | 7/2008 | Watlington et al. | |
| 2008/0243163 A1 | * | 10/2008 | Masseglia et al. | 606/185 |
| 2009/0171360 A1 | * | 7/2009 | Whelan | 606/88 |
| 2009/0265002 A1 | * | 10/2009 | Re et al. | 623/13.14 |
| 2009/0265003 A1 | * | 10/2009 | Re et al. | 623/13.14 |

OTHER PUBLICATIONS

International Search Report from International Application PCT/US2009/066580 having a mailing date of Jun. 25, 2010.
Written Opinion of the International Searching Authority from International Application PCT/US2009/066580 having a mailing date of Jun. 25, 2010.

(Continued)

*Primary Examiner* — Suzette J Gherbi
(74) *Attorney, Agent, or Firm* — O'Brien Jones PLLC

(57) ABSTRACT

A drill bit comprising a trocar tip on an end of a fluted portion is disclosed. The trocar tip may configured to cut through relatively hard bone. The drill bit may also have a fluted portion for cutting through softer bone.

23 Claims, 2 Drawing Sheets

OTHER PUBLICATIONS

"Basic Information on the Surgical Procedure," manual, Jan. 2007, 64 pp., Straumann, Basel, Switzerland.

"Basic Information on the Surgical Procedures," manual. Sep. 2007, 79 pp., Straumann, Basel, Switzerland.

"Precise Depth Control," brochure, undated, 8 pp., Straumann, Basel, Switzerland.

"SPI® System—Design Concept," brochure, May 2005, 28 pp., Thommen Medical AG, Waldenburg, Switzerland.

* cited by examiner

TROCAR-TIPPED DRILL BIT

TECHNICAL FIELD

The present disclosure relates generally to drill bits for use in medical procedures.

BACKGROUND

Since the discovery that titanium can fuse to bone, titanium dental implants have represented a growing field of dental reconstruction technology for replacing natural teeth. During implantation, a hole is drilled through the bone after the tissue has been retracted or through the gingiva, the gums surrounding the root of a tooth, and into the jawbone. A titanium or titanium alloy implant is then fixed within the hole of the jawbone. Over a period of months, the titanium implant fuses to the jawbone through a process called osseointegration. A replacement tooth can then be attached to the implant.

The human jaw comprises two types of bone. A very hard, dense cortical bone layer surrounds an interior of softer cancellous bone. Conventional implantation techniques require several steps involving the use of a series of drill bits to form the hole in the jawbone where the titanium implant will be located. In a first step, a round burr drill bit is used to penetrate the hard outer cortical bone. Second, a standard, fluted twist drill bit is used to create a hole in the softer bone for the implant. Next, a series of holes of increasing diameter are subsequently formed using fluted twist drill bits having increasing diameters, until the desired implant hole size is achieved. Typical diameters for the fluted twist drill bits include, for example, 2.2 mm, 2.8 mm, 3.5 mm, and 4.2 mm. A countersink drill bit, also known as a pilot or step drill bit, may be used to broaden the opening of the hole to the diameter of the next larger fluted twist drill bit. An optional further step of tapering the top of the hole may also be performed using a countersink drill bit, also known as a profile drill bit, depending on how the implant is to be placed within the bone, for example, if the coronal neck of the implant is placed flush with the bone.

Thus, conventional implant procedures require a series of drillings beginning with the cutting of the cortical bone followed by a series of drillings to form and expand the hole. In traditional implant procedures, a total of five or more drill bits, including the burr drill bit, may be used to place a single implant. For patients, especially those requiring multiple implants, the need to use multiple drill bits may result in a very long and uncomfortable multiple-step procedure. Similar multiple-step drilling procedures are also used in other medical procedures that require drilling in bone. Thus, there is a long-felt need in the industry for a tool that can reduce the number of steps and/or drill bits in such procedures.

Although the present disclosure may obviate one or more of the above-mentioned disadvantages, it should be understood that some aspects of the invention might not necessarily obviate one or more of those disadvantages.

SUMMARY

In accordance with various exemplary embodiments, the present teachings contemplate drill bits having a trocar tip for use in medical procedures. Drill bits according to various embodiments of the invention may further comprise a countersink. Drill bits as described herein may, for example when used in performing dental procedures, can cut through both the cortical bone and the cancellous bone, and may therefore reduce the number of steps and/or drill bits needed for such procedures.

The term "trocar tip" as used herein may refer to a tip formed by a plurality of sides ending in a point. By way of example only, a trocar tip may comprise the form of a three-sided pyramid. In various exemplary embodiments, the trocar tip may be capable of penetrating and cutting cortical bone. In various exemplary embodiments, the drill bits having a trocar tip may be used in medical procedures that require drilling through other types of bone.

The term "drill bit" as used herein may refer to a tool meant to cut holes by rotating around an axis, such as, for example, a central, longitudinal axis. The term drill bit encompasses, for example, dental burrs and medical tools designed to create holes in bone and other tissue.

The term "countersink drill bit" as used herein may refer to a tool meant to broaden the opening of a hole, increase the diameter of a hole for a subsequent drill bit, or provide a guide for determining the depth of the hole. Thus, the term "countersink drill bit" as used herein encompasses drill bits that provide the function of drill bits known as pilot drill bits, step drill bits, and stop drill bits.

In the following description, certain aspects and embodiments will become evident. It should be understood that the invention, in its broadest sense, could be practiced without having one or more features of these aspects and embodiments. It should be understood that these aspects and embodiments are merely exemplary and explanatory and are not restrictive of the present teachings or claims.

BRIEF DESCRIPTION OF THE DRAWINGS

The following figures, which are incorporated in and constitute a part of the specification, serve to further illustrate exemplary embodiments of the present teachings. The figures are not, however, intended to be restrictive of the present teachings or claims. In the drawings.

DETAILED OF EXEMPLARY EMBODIMENTS

Figure 1:
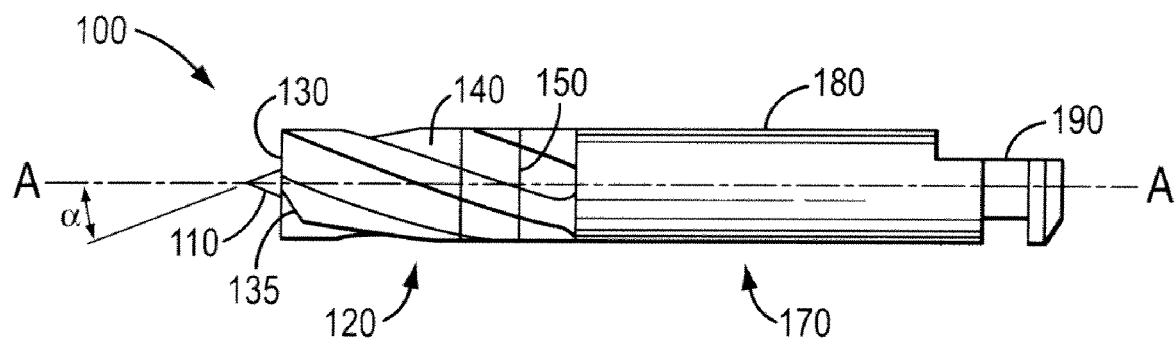
FIG. 1 is a side view of a drill bit according to an exemplary embodiment of the present teachings.

Reference will now be made to various exemplary embodiments, at least one example of which is illustrated in the accompanying figures. However, these various exemplary embodiments are not intended to limit the disclosure. To the contrary, the disclosure is intended to cover alternatives, modifications, and equivalents.

The present disclosure contemplates various exemplary embodiments for a drill bit having a trocar tip. The drill bit may be used to perform medical procedures, such as, for example, dental procedures. For example, the drill bit may be used for implanting dental implants. While not wishing to be bound by theory, it is believed that in procedures for implanting dental implants, the trocar tip not only cuts through the hard, cortical bone, but also stabilizes other portions of the drill bit as they are cutting by acting as a guide.

According to various exemplary embodiments of the present disclosure, the drill bit may comprise at least one material chosen from metals and ceramic. Examples of metals that may be used include, by way of example only, stainless steel, high speed steel, and carbide alloys. In at least one embodiment, the drill bit may comprise two or more different materials. It is well within the ability of those ordinarily skilled in the art to determine whether a material is suitable for the drill bit, taking into consideration, for example, the intended use of the drill bit, whether it will be used once and discarded or reusable, etc.

In various exemplary embodiments, the drill bit may have coatings formed on the surface thereof. For example, the drill bit may have a carbide or diamond coating, chrome plating, titanium nitride, or any other coating known to those ordinarily skilled in the art. In at least one embodiment, the drill bit may have a tungsten carbide coating. In at least one further embodiment of the present disclosure, the drill bit may comprise a coating on the cutting surfaces of the drill bit.

The drill bit according to various embodiments may comprise a plurality of lengths and diameters. For example, the drill bit may have a cutting length, i.e., the depth of the hole formed by the drill bit, ranging from about 6 mm to about 10 mm, or may be shorter or longer. For example, the drill bit may have a cutting length of about 14 mm. Drill bits of any cutting length are contemplated, and the appropriate length may be selected based on, for example, the intended use of the drill bit. According to at least one exemplary embodiment, the drill bit may have a diameter ranging from about 2.2 mm to about 4.2 mm. Drill bits having a smaller or larger diameter are also contemplated and the diameter may be chosen according to, for example, the intended use of the drill bit.

The trocar tip according to at least one embodiment of the present disclosure comprises a plurality of sides terminating in a point. The sides of the trocar tip may be, for example, curved or straight.

The appropriate length of the trocar tip may depend on, in various embodiments, the thickness of the cortical bone to be cut. For example, a trocar tip having a length of about 0.6 mm (i.e., measured along a longitudinal axis of the drill bit, such as axis A shown in FIG. 1) can be used in various exemplary embodiments to cut through the cortical bone of an average jaw. In one exemplary embodiment, the length of the trocar tip may be more or less, for example depending on the thickness of the cortical bone.

The appropriate number of sides and angle of the sides of the trocar tip may vary, for example depending on the intended use of the drill bit. It is well within the ability of those having ordinary skill in the art to determine the optimal number and angle of the sides of the trocar tip for any particular application. For example, the number and angle of the sides may be determined according to the thickness of the cortical bone to be bored. In one exemplary embodiment, a trocar tip may have three sides. In a further exemplary embodiment, the sides of the trocar tip may be formed at an angle of about 5° to about 15° relative to the longitudinal axis and cutting edge of the drill bit. For example, the angle of the sides may be about 8° relative to the longitudinal axis of the drill bit.

In at least one embodiment of the present disclosure, the drill bit comprises a trocar tip and a fluted portion. An example of a drill bit comprising a trocar tip and a fluted portion is shown in FIG. 1. In FIG. 1, exemplary drill bit 100 comprises a trocar tip 110 at one end of the drill bit along a longitudinal axis A. Trocar tip 110 terminates in a point and has sides tapered at an angle α relative to longitudinal axis A.

Drill bit 100 may further comprise a fluted portion 120, having a plurality of flutes 140. Fluted portion 120 may be, for example, cylindrical or frustoconical in shape, i.e., the fluted portion may have straight or tapered sides. Drill bit 100 may comprise any number of flutes 140, such as, for example, from 2 to 6 flutes. Flutes 140 may be formed in any pattern, such as a helical pattern as shown in FIG. 1. In other embodiments, the flutes may be formed in other patterns, such as, for example, parallel to axis A.

Adjacent trocar tip 110, fluted portion 120 terminates in primary cutting edges 130, with one primary cutting edge for each flute in the fluted portion, wherein the primary cutting edges may optionally be in a plane substantially perpendicular to axis A. Primary cutting edges 130 may be formed with a cutting angle, for example, ranging from about 5° to about 20° with respect to a plane perpendicular to axis A. Without wishing to be limited by theory, it is believed that forming the primary cutting edges substantially perpendicular to axis A reduces the production of heat and vibration during drilling. The cross-sectional area of primary cutting edges 130 within a plane perpendicular to axis A is greater than the largest cross-sectional area of trocar tip 110 taken in any plane perpendicular to axis A. Thus, primary cutting edges 130 radially extend further from axis A than trocar tip 110.

Secondary cutting edges 135 may optionally be positioned between primary cutting edges 130 and the remainder of the flutes 140. Secondary cutting edges 135 may have a cuffing angle, for example ranging from about 25° to about 50° relative to the plane perpendicular to axis A.

Drill bit 100 may optionally comprise at least one depth marking 150. Depth markings 150 indicate how far drill bit 100 has penetrated. While the markings may be made in any known fashion, in at least one embodiment, depth markings 150 are marked by laser. Depth markings may be made at any desired location on the drill bit.

Drill bit 100 may also comprise a shank portion 170 at an end opposite trocar tip 110, which may optionally comprise a shaft 180 and a locking portion 190. Shaft 180 may be straight or tapered. Locking portion 190 may be designed to matingly fit to a drill engine, such as, for example, a dental handpiece. Locking portion 190, may be, for example, a dental "T" latch, a surgical J notch, or friction fitting. One skilled in the art would recognize that the present disclosure encompasses other locking portions and that the choice of locking portion depends on the intended use of the drill bit.

Figure 2:
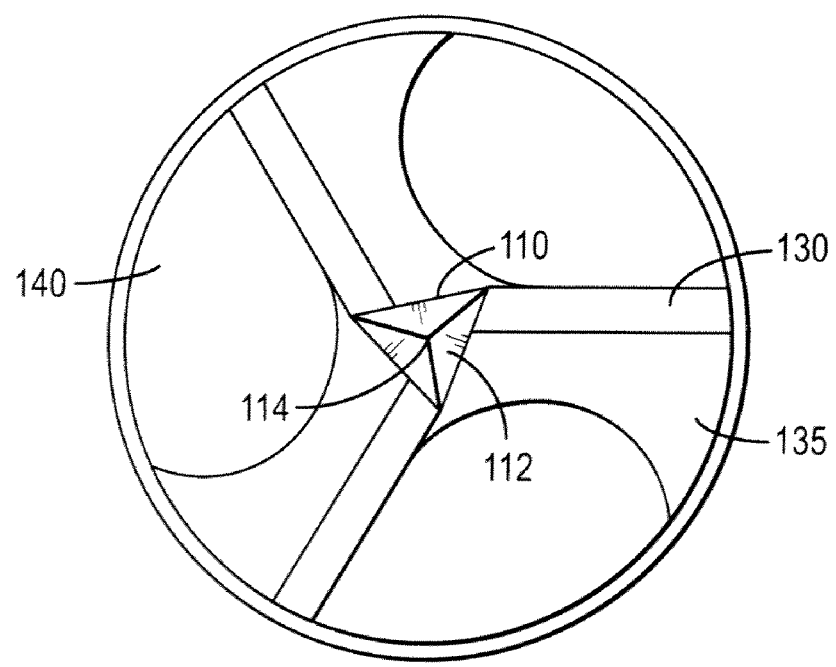
FIG. 2 is an end view of the drill bit of FIG. 1 looking along the axis A from the trocar-tipped end of the drill bit.

FIG. 2 is a view of exemplary drill bit 100 as viewed in a direction along axis A from the trocar-tipped end of the drill bit 100. As seen in FIG. 2, trocar tip 110 is pyramidal in shape and comprises three sides 112 that meet at point 114. Sides 112 may be planar or curved. Trocar tip 110 may comprise any number of sides, such as, for example, from 3 to 8 sides or more, depending upon the intended application. FIG. 2 also shows primary and secondary cutting edges 130 and 135, as well as the curved flutes 140.

Figure 3:
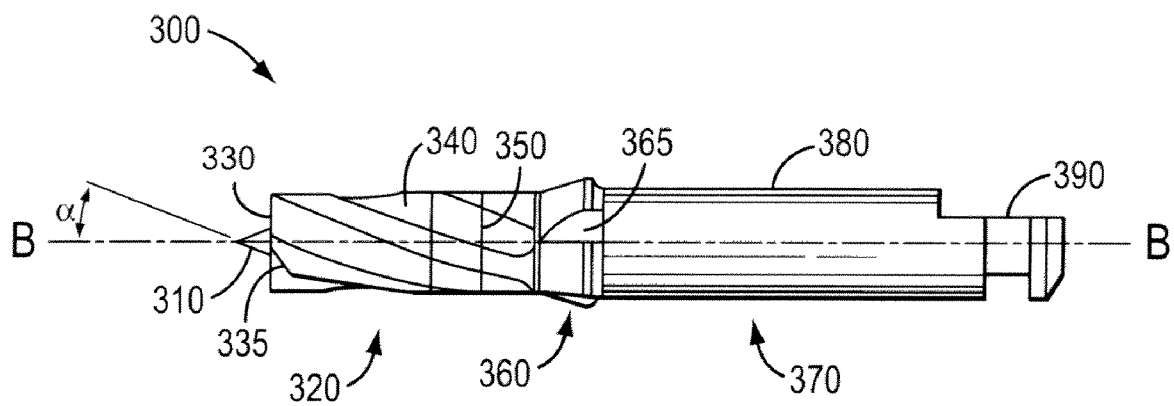
FIG. 3 is a side view of a drill bit according to another exemplary embodiment of the present disclosure.

In at least one embodiment of the present disclosure, the trocar-tipped drill bit may comprise a countersink portion. FIG. 3 shows an exemplary drill bit 300 comprising trocar tip 310, fluted portion 320, and countersink portion 360. The sides of trocar tip 310 are tapered at an angle α relative to longitudinal axis B.

Fluted portion 320 may comprise a plurality of flutes 340 that may terminate in primary cutting edges 330 and secondary cutting edges 335. Depth markings 350 mark different cutting depths along the length of drill bit 300.

Countersink portion 360 may be tapered and may comprise flutes 365. The tapered edges of countersink portion 360 may allow the opening of the hole to be enlarged.

Drill bit 300 also comprises shank portion 370, which has a shaft 380 and fitting portion 390 for attachment to a drill engine, e.g., a dental handpiece.

Figure 4:
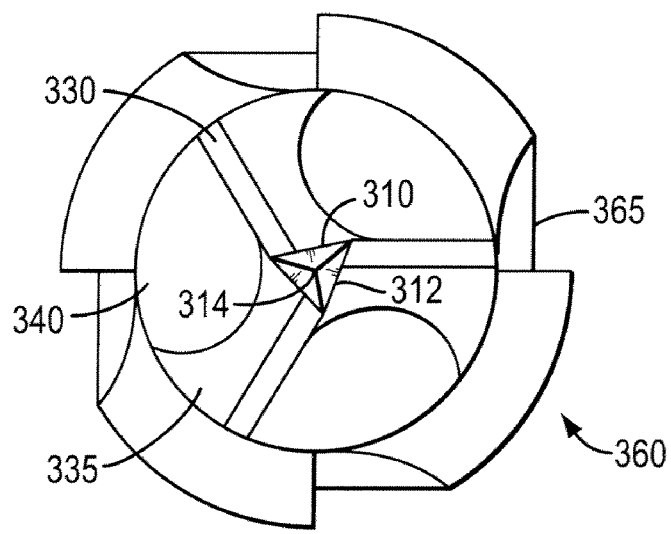
FIG. 4 is an end view of the drill bit of FIG. 3 looking in along the axis B from the trocar-tipped end of the drill bit.

A view of exemplary drill bit 300 along longitudinal axis B and from the trocar-tipped end of the drill bit 300 is shown in FIG. 4. FIG. 4 shows trocar tip 370 having sides 312 meeting at point 314. Curved flutes 340 may terminate in primary and secondary cutting edges 330 and 335, respectively. Countersink portion 360 may comprise a plurality of flutes 365 for enlarging the opening of the hole.

Figure 5:
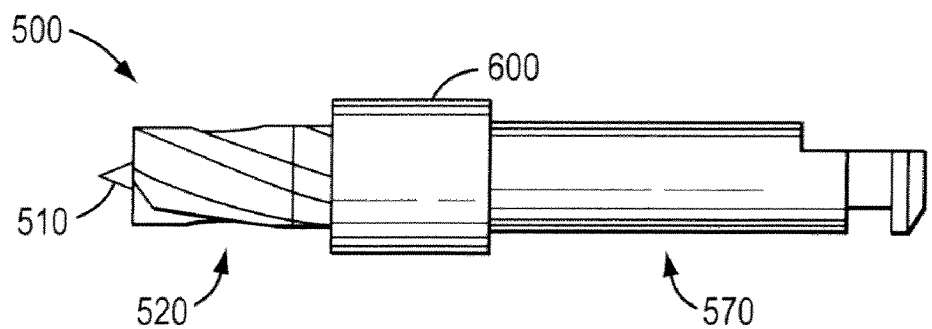
FIG. 5 is a side view of a drill bit with a sleeve according to an exemplary embodiment of the present disclosure.

In at least one embodiment of the present disclosure, the drill bit may further comprise a sleeve that covers at least a portion of the drill bit to control the depth of penetration through or into the bone. For example, with reference to FIG. 5, an exemplary drill bit 500 comprises trocar tip 510, fluted portion 520, and shank portion 570. Sleeve 600 is fitted over the drill bit 500 to control the depth of the drilling. The sleeve 600 may be permanently or temporarily attached to the drill bit 500. For example, the sleeve 600 may be either permanently or temporarily adhered to the drill bit 500, or the sleeve 600 may snap on the drill bit. The sleeve 600 may be formed of any suitable material or materials, such as, for example, metal, ceramic, and/or plastic.

In exemplary embodiments comprising a countersink, the length and angle of the countersink may be selected according to the intended use of the drill bit. For example, the size and angle of the countersink may be selected to match the shape of a dental implant. By way of example only, a 2.2 mm diameter drill bit may have a countersink with a length of about 1.8 mm and a taper angle of about 18° to about 80° relative to the central axis of the drill bit. In one exemplary embodiment, the taper angle of the countersink may be about 33° relative to the central axis of the drill bit. The angle of the countersink may also vary based on the diameter of the drill bit.

In various exemplary embodiments, drill bits according to the present disclosure may be used in series to sequentially expand the diameter of the hole. In at least one embodiment, each of the drill bits may have a trocar tip. Alternatively, only the drill bits cuffing through cortical bone may have a trocar tip. Alternatively, in various embodiments, the hole for the implant can be formed using a single drill bit that cuts through the cortical bone and the cancellous bone and has a diameter corresponding to the diameter of the implant being used. In various exemplary embodiments, when the drill bit has a countersink, a single drill bit may form an enlarged opening via the countersink portion that may allow an implant to be inserted below the bone.

The present teachings also contemplate a method for drilling holes in cortical and/or cancellous bone, as well as drilling in soft tissues.

In at least one exemplary embodiment, a method for drilling holes in cortical and/or cancellous bone includes drilling through cortical bone and/or soft tissue with a trocar tip disposed on an end of a drill bit and optionally drilling through cancellous bone with a fluted portion of the drill bit. The trocar tip may guide and stabilize the fluted portion. The method may further include enlarging the hole opening with a countersink portion of the drill bit. The entire procedure of drilling through the cortical bone and/or soft tissue, drilling through the cancellous bone, and enlarging the hole opening can be performed without retracting the drill bit until the hole opening has been enlarged. In at least one embodiment, the cortical bone and/or cancellous bone comprises a portion of a human jawbone.

It is noted that, as used in this specification and the appended claims, the singular forms "a," "an," and "the," include plural referents unless expressly and unequivocally limited to one referent. Thus, for example, reference to "a flute" can refer to one, two, or more flutes. As used herein, the term "include" and its grammatical variants are intended to be non-limiting, such that recitation of items in a list is not to the exclusion of other like items that can be substituted or added to the listed items.

It will be apparent to those skilled in the art that various modifications and variation can be made to the drill bits and methods of the present disclosure without departing from the scope its teachings. Other embodiments of the disclosure will be apparent to those skilled in the art from consideration of the specification and practice of the teachings disclosed herein. It is intended that the embodiments described in the specification be considered as exemplary only.

What is claimed is:

1. A drill bit for drilling through bone, the drill bit comprising:
   a fluted portion comprising a plurality of flutes; and
   a trocar tip disposed at an end of the fluted portion, wherein the trocar tip comprises a tapered, non-fluted lateral outer surface, and
   wherein each of the plurality of flutes comprises a primary cutting edge between the trocar tip and a remainder of the fluted portion.

2. The drill bit of claim 1, wherein the lateral outer surface comprises a plurality of sides that are curved or planar.

3. The drill bit of claim 2, wherein the trocar tip comprises from 3 to 8 sides.

4. The drill bit of claim 2, wherein the plurality of sides taper at an angle ranging from about 5° to about 15° relative to a longitudinal axis of the drill bit.

5. The drill bit of claim 1, wherein the plurality of cutting edges are in a plane substantially perpendicular to a longitudinal axis of the drill bit.

6. The drill bit of claim 1, wherein each of the plurality of cutting edges has a cutting angle ranging from about 5° to about 20° with respect to a plane perpendicular to a longitudinal axis of the drill bit.

7. The drill bit of claim 1, further comprising additional cutting edges positioned between the plurality of primary cutting edges and the remainder of the fluted portion.

8. The drill bit of claim 1, wherein each of the additional cutting edges has a cutting angle ranging from about 25° to about 50° with respect to a plane perpendicular to a longitudinal axis of the drill bit.

9. The drill bit of claim 1, further comprising a countersink portion disposed at an end of the fluted portion opposite the trocar tip.

10. The drill bit of claim 9, wherein the countersink portion is tapered at an angle ranging from about 18° to about 80° relative to a longitudinal axis of the drill bit.

11. The drill bit of claim 1, further comprising a sleeve configured to be disposed relative to the drill bit to limit a penetration depth of the drill bit during drilling.

12. The drill bit of claim 1, wherein the trocar tip is configured to drill through relatively hard bone and the fluted portion is configured to drill through relatively soft bone.

13. The drill bit of claim 12, wherein the trocar tip is configured to drill through cortical bone and the fluted portion is configured to drill through cancellous bone.

14. The drill bit of claim 1, wherein the trocar tip is disposed at an end face of the fluted portion, the end face having a perimeter that is located beyond the lateral outer surface of the trocar tip in a radial direction from a longitudinal axis of the drill bit.

15. A method for drilling a hole for receiving a dental implant, the method comprising:

drilling through at least one of cortical bone and soft tissue with a trocar tip disposed on an end of a drill bit, wherein the trocar tip comprises a tapered, non-fluted lateral outer surface;

drilling through cancellous bone with a fluted portion of the drill bit; and stabilizing the drill bit with the trocar tip during the drilling through the cancellous bone.

16. The method of claim 15, further comprising enlarging a hole formed during the drilling through the cancellous bone with a countersink portion disposed on an end of the drill bit opposite to the end on which the trocar tip is disposed.

17. A drill bit for drilling through bone, the drill bit comprising:

a fluted portion that terminates in an end face that is substantially perpendicular to a longitudinal axis of the drill bit; and a trocar tip disposed at the end face of the fluted portion, wherein the trocar tip has a pointed tip at a first end and a base at a second end, and wherein a perimeter of the base is smaller than a perimeter of the end face.

18. The drill bit of claim 17, wherein the perimeter of the end face is located beyond the perimeter of the base in a radial direction from the longitudinal axis of the drill bit.

19. The drill bit of claim 17, wherein the end face comprises a plurality of primary cutting edges.

20. The drill bit of claim 19, wherein a cross-sectional area of the plurality of primary cutting edges within a plane perpendicular to the longitudinal axis of the drill bit is greater than the largest cross-sectional area of the trocar tip taken in any plane perpendicular to the longitudinal axis of the drill bit.

21. The drill bit of claim 17, wherein the trocar tip comprises a lateral outer surface that tapers from the base to the pointed end.

22. The drill bit of claim 21, wherein the lateral outer surface is non-fluted.

23. The drill bit of claim 21, wherein the lateral outer surface comprises a plurality of planar or curved sides.

* * * * *